US005650391A

United States Patent [19]
Schwartz et al.

[11] Patent Number: 5,650,391
[45] Date of Patent: Jul. 22, 1997

[54] METHODS AND COMPOSITIONS FOR INHIBITION OF HEPATIC CLEARANCE OF TISSUE FACTOR PATHWAY INHIBITOR

[75] Inventors: Alan L. Schwartz, Clayton; Ilka Warshawsky, St. Louis; George J. Broze, Ladue, all of Mo.

[73] Assignee: Jewish Hospital of St. Louis, St. Louis, Mo.

[21] Appl. No.: 216,593

[22] Filed: Mar. 21, 1994

[51] Int. Cl.$^6$ ................................................ A61K 38/16
[52] U.S. Cl. ............................................... 514/12; 514/2
[58] Field of Search ......................... 514/2, 12; 435/69.1, 435/69.2

[56] References Cited

U.S. PATENT DOCUMENTS

| 5,312,736 | 5/1994 | Rasmussen et al. | 435/69.2 |
| 5,474,766 | 12/1995 | Schwartz et al. | 514/12 |

OTHER PUBLICATIONS

Warshawsky et al., *J. Clin. Invest.*, 92, 937–944 (1993).

Iadonato et al., *Biochem. J.*, 296, 867–875 (1993).

Warshawsky et al., *J. Biol. Chem.*, 268, 22046–22054 (1993).

Bu et al., *J. Biol. Chem.*, 268, 13002–13009 (1993).

Bu et al., *Proc. Natl. Acad. Sci. USA*, 89, 7427–7431 (1992).

Smith et al *J Biol Chem* 267 19140–46 (1992).

*Primary Examiner*—Marianne P. Allen
*Assistant Examiner*—Stephen Gucker
*Attorney, Agent, or Firm*—Dennis A. Bennett

[57] ABSTRACT

The present invention discloses methods and compositions for inhibiting the hepatic clearance of Tissue Factor Pathway Inhibitor (TFPI) using receptor-associated protein.

6 Claims, 6 Drawing Sheets

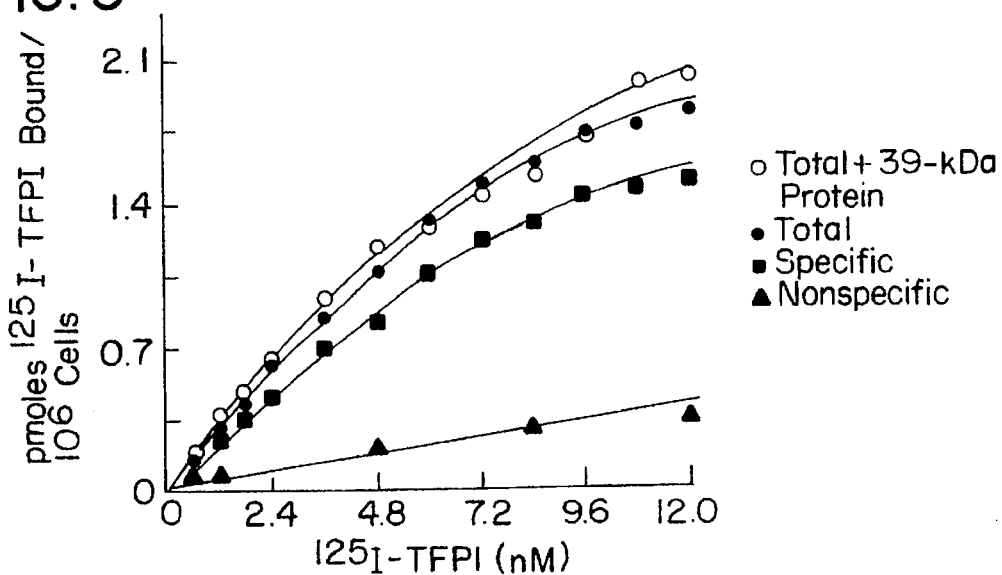
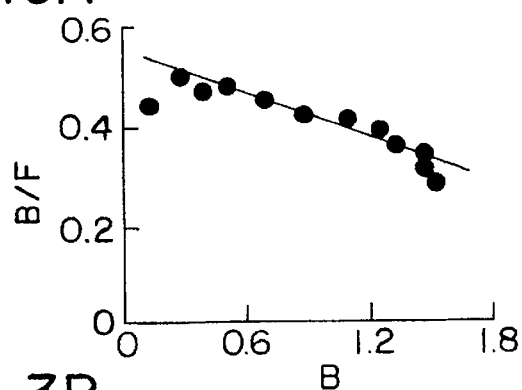
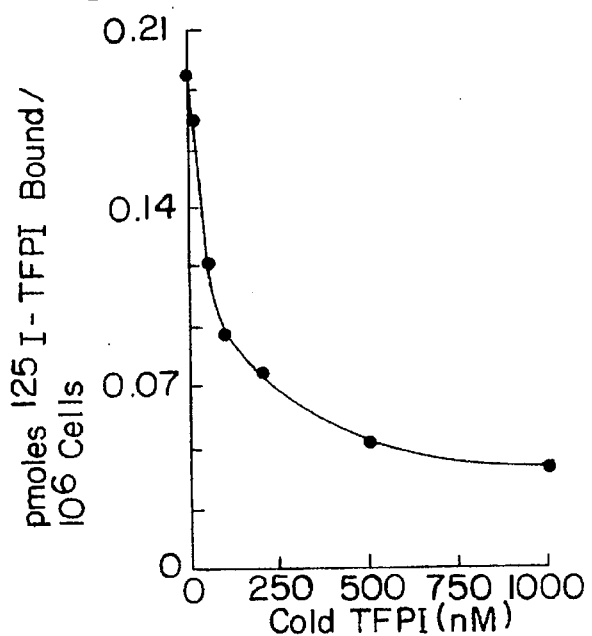

- △ Surface −39-kDa Protein
- ▲ Surface +39-kDa Protein
- □ Dissociated −39-kDa Protein
- ■ Dissociated +39-kDa Protein

- ○ Degraded −39-kDa Protein
- ● Degraded +39-kDa Protein

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 323 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Tyr Ser Arg Glu Lys Asn Gln Pro Lys Pro Ser Pro Lys Arg Glu Ser
 1               5                  10                  15
Gly Glu Glu Phe Arg Met Glu Lys Leu Asn Gln Leu Trp Glu Lys Ala
                20                  25                  30
Gln Arg Leu His Leu Pro Pro Val Arg Leu Ala Glu Leu His Ala Asp
                35                  40                  45
Leu Lys Ile Gln Glu Arg Asp Glu Leu Ala Trp Lys Lys Leu Lys Leu
            50                  55                  60
Asp Gly Leu Asp Glu Asp Gly Glu Lys Glu Ala Arg Leu Ile Arg Asn
 65                 70                  75                  80
Leu Asn Val Ile Leu Ala Lys Tyr Gly Leu Asp Gly Lys Lys Asp Ala
                    85                  90                  95
Arg Gln Val Thr Ser Asn Ser Leu Ser Gly Thr Gln Glu Asp Gly Leu
                100                 105                 110
Asp Asp Pro Arg Leu Glu Lys Leu Trp His Lys Ala Lys Thr Ser Gly
            115                 120                 125
Lys Phe Ser Gly Glu Glu Leu Asp Lys Leu Trp Arg Glu Phe Leu His
    130                 135                 140
His Lys Glu Lys Val His Glu Tyr Asn Val Leu Leu Glu Thr Leu Ser
145                 150                 155                 160
Arg Thr Glu Glu Ile His Glu Asn Val Ile Ser Pro Ser Asp Leu Ser
                165                 170                 175
Asp Ile Lys Gly Ser Val Leu His Ser Arg His Thr Glu Leu Lys Glu
                180                 185                 190
Lys Leu Arg Ser Ile Asn Gln Gly Leu Asp Arg Leu Arg Arg Val Ser
            195                 200                 205
His Gln Gly Tyr Ser Thr Glu Ala Glu Phe Glu Glu Pro Arg Val Ile
    210                 215                 220
Asp Leu Trp Asp Leu Ala Gln Ser Ala Asn Leu Thr Asp Lys Glu Leu
225                 230                 235                 240
Glu Ala Phe Arg Glu Glu Leu Lys His Phe Glu Ala Lys Ile Glu Lys
                245                 250                 255
His Asn His Tyr Gln Lys Gln Leu Glu Ile Ala His Glu Lys Leu Arg
                260                 265                 270
His Ala Glu Ser Val Gly Asp Gly Glu Arg Val Ser Arg Ser Arg Glu
            275                 280                 285
Lys His Ala Leu Leu Glu Gly Arg Thr Lys Glu Leu Gly Tyr Thr Val
    290                 295                 300
Lys Lys His Leu Gln Asp Leu Ser Gly Arg Ile Ser Arg Ala Arg His
305                 310                 315                 320
Asn Glu Leu
```

( 2 ) INFORMATION FOR SEQ ID NO:2:

( i ) SEQUENCE CHARACTERISTICS:
        ( A ) LENGTH: 209 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Pro  Arg  Leu  Glu  Lys  Leu  Trp  His  Lys  Ala  Lys  Thr  Ser  Gly  Lys  Phe
 1              5                   10                            15

Ser  Gly  Glu  Glu  Leu  Asp  Lys  Leu  Trp  Arg  Glu  Phe  Leu  His  His  Lys
              20                   25                       30

Glu  Lys  Val  His  Glu  Tyr  Asn  Val  Leu  Leu  Glu  Thr  Leu  Ser  Arg  Thr
         35                       40                       45

Glu  Glu  Ile  His  Glu  Asn  Val  Ile  Ser  Pro  Ser  Asp  Leu  Ser  Asp  Ile
    50                        55                   60

Lys  Gly  Ser  Val  Leu  His  Ser  Arg  His  Thr  Glu  Leu  Lys  Glu  Lys  Leu
 65                       70                   75                            80

Arg  Ser  Ile  Asn  Gln  Gly  Leu  Asp  Arg  Leu  Arg  Arg  Val  Ser  His  Gln
              85                       90                        95

Gly  Tyr  Ser  Thr  Glu  Ala  Glu  Phe  Glu  Glu  Pro  Arg  Val  Ile  Asp  Leu
             100                      105                       110

Trp  Asp  Leu  Ala  Gln  Ser  Ala  Asn  Leu  Thr  Asp  Lys  Glu  Leu  Glu  Ala
             115                      120                      125

Phe  Arg  Glu  Glu  Leu  Lys  His  Phe  Glu  Ala  Lys  Ile  Glu  Lys  His  Asn
     130                      135                      140

His  Tyr  Gln  Lys  Gln  Leu  Glu  Ile  Ala  His  Glu  Lys  Leu  Arg  His  Ala
145                           150                      155                 160

Glu  Ser  Val  Gly  Asp  Gly  Glu  Arg  Val  Ser  Arg  Ser  Arg  Glu  Lys  His
                  165                      170                      175

Ala  Leu  Leu  Glu  Gly  Arg  Thr  Lys  Glu  Leu  Gly  Tyr  Thr  Val  Lys  Lys
               180                      185                      190

His  Leu  Gln  Lys  Leu  Ser  Gly  Arg  Ile  Ser  Arg  Ala  Arg  His  Asn  Glu
          195                      200                      205

Leu
```

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CGCGTGGATC CCCCAGGCTG GAAAAGCTGT GG                         32

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

-continued ( x i ) SEQUENCE DESCRIPTION: SEQ ID NO:4:

CGAGCCGTGT TACTCGAGAC TCTTAAGTAG CA                                    3 2

( 2 ) INFORMATION FOR SEQ ID NO:5:

( i ) SEQUENCE CHARACTERISTICS:
        ( A ) LENGTH: 203 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Pro Arg Leu Glu Lys Leu Trp His Lys Ala Lys Thr Ser Gly Ser Val
 1               5                  10                  15
Arg Leu Thr Ser Cys Ala Arg Val Leu His Lys Glu Lys Ile His Glu
             20                  25                  30
Tyr Asn Val Leu Leu Asp Thr Leu Ser Arg Ala Glu Glu Gly Tyr Glu
         35                  40                  45
Asn Leu Leu Ser Pro Ser Asp Met Thr His Ile Lys Ser Asp Thr Leu
     50                  55                  60
Ala Ser Lys His Ser Glu Leu Lys Asp Arg Leu Arg Ser Ile Asn Gln
 65                  70                  75                  80
Gly Leu Asp Arg Leu Arg Lys Val Ser His Gln Leu Arg Pro Ala Thr
             85                  90                  95
Glu Phe Glu Glu Pro Arg Val Ile Asp Leu Trp Asp Leu Ala Gln Ser
            100                 105                 110
Ala Asn Phe Thr Glu Lys Glu Leu Glu Ser Phe Arg Glu Glu Leu Lys
        115                 120                 125
His Phe Glu Ala Lys Ile Glu Lys His Asn His Tyr Gln Lys Gln Leu
    130                 135                 140
Glu Ile Ser His Gln Lys Leu Lys His Val Glu Ser Ile Gly Asp Pro
145                 150                 155                 160
Glu His Ile Ser Arg Asn Lys Glu Lys Tyr Val Leu Leu Glu Glu Lys
                165                 170                 175
Thr Lys Glu Leu Gly Tyr Lys Val Lys Lys His Leu Gln Asp Leu Ser
            180                 185                 190
Ser Arg Val Ser Arg Ala Arg His Asn Glu Leu
        195                 200
```

METHODS AND COMPOSITIONS FOR INHIBITION OF HEPATIC CLEARANCE OF TISSUE FACTOR PATHWAY INHIBITOR

This invention was made with government support under grant numbers HL 17646, HL 34462, and HL 07275 awarded by the NIH. The government may have certain rights in this invention.

FIELD OF THE INVENTION

This invention relates to methods and compositions for inhibiting the hepatic clearance of Tissue Factor Pathway Inhibitor (TFPI).

BACKGROUND OF THE INVENTION

Tissue factor (TF)[1] is a 45-kDa integral membrane glycoprotein that is an essential cofactor in initiating the extrinsic pathway of blood coagulation. In response to blood vessel injury, TF, which is produced constitutively by cells that are separated from blood by the vascular endothelium, gains access to the plasma. Plasma factor VII or VIIa binds TF and the resulting factor VIIa-TF complex activates factors X to Xa and IX to IXa. This eventually leads to the generation of thrombin and the formation of a fibrin clot. TF-induced blood coagulation is primarily regulated by tissue factor pathway inhibitor (TFPI), a 42-kDa plasma glycoprotein also referred to as lipoprotein-associated coagulation inhibitor (LACI) and extrinsic pathway inhibitor (EPI). TFPI contains an acidic amino-terminal domain followed by three tandem Kunitz-type protease inhibitory domains and a basic carboxy-terminal domain. Inhibition of TF-induced blood coagulation by TFPI involves a two step reaction leading to the formation of a quaternary factor Xa-TFPI-factor VIIa-TF complex. In the first step factor Xa binds to the second Kunitz domain of TFPI and in the second step, TFPI-factor Xa binds to the TF-factor VIIa complex through an interaction between the first Kunitz domain of TFPI and factor VIIa (reviewed in Refs. 1,2).

A wide range of plasma TFPI concentrations is found in normal individuals with a mean of ~2.5 nM (3). Greater than 90% of this TFPI is bound to lipoproteins (low density lipoprotein>high density lipoprotein>very low density lipoprotein), (4,5). Plasma TFPI levels increase several fold following the infusion of heparin (6,7). TFPI is thought to be released from the vascular endothelium where it may be bound to heparan sulfate or glycosaminoglycans.

Several animal studies have shown that recombinant TFPI is effective against TF-induced coagulopathy (8), prevents arterial thrombosis (9), and reduces mortality from bacterial septic shock (10). Pharmacokinetic studies (11) following an intravenous bolus injection of recombinant TFPI in rabbits have shown that TFPI clearance from the plasma is a biphasic process with half-lives of 2.3 min and 79 min. The primary organs involved in TFPI clearance are the liver and kidney (especially the outer cortex).

The low density lipoprotein receptor-related protein/$a_2$-macroglobulin receptor (LRP) and glycoprotein 330 (gp330) are two members of the low density lipoprotein receptor family involved in the endocytosis of several circulating plasma proteins. The endocytic function of LRP appears to be predominantly in the liver whereas that of gp330 is in the kidney (reviewed in Ref. 12). LRP and gp330 bind similar ligands including complexes between plasminogen activator inhibitor type 1(PAI-1) and tissue-type (t-PA) or urokinase-type (u-PA) plasminogen activators, β-migrating very low density lipoproteins (βVLDL) complexed with apolipoprotein (apo) E, lipoprotein lipase, and lactoferrin (13–15). In addition, LRP binds $\alpha_2$-macroglobulin-protease complexes $\alpha_2$m*) (16–18) and *Pseudomonas exotoxin A* (19). A 39-kDa protein, also termed receptor-associated protein (RAP), copurifies with both LRP and gp330 (16,20). This 39-kDa protein is a potent inhibitor of all known ligand interactions with LRP and gp330, as shown by ligand blotting experiments and by binding and uptake experiments in cultured cells (13,14,19,21–24). It has been recently reported that intravenous administration of the 39-kDa protein to rats prolonged the plasma half-life of t-PA from 1 min to ~6–9 min. It was also found that the 39-kDa protein itself was rapidly cleared from the circulation, with the liver and outer cortex of the kidney being the primary sites of clearance (25). Although the in vivo physiological role of the 39-kDa protein at present is not clear, it has been postulated to function as a regulator of LRP and gp330 activity.

SUMMARY OF THE INVENTION

The present invention discloses a novel method of inhibiting the hepatic clearance of TFPI in vivo, preferably in humans, by the administration of the receptor-associated protein (RAP) or a fragment thereof to a patient receiving treatment with TFPI.

The present invention also provides a pharmaceutical composition which includes TFPI and RAP.

It is an object of the present invention to significantly increase the plasma half life of TFPI.

Another object of the present invention is to reduce the amount of TFPI administered to a mammal or patient in need of TFPI and still achieve the needed physiological results as would be achieved using a higher dosage of TFPI. By lowering the amount of TFPI needed a cost saving can be realized and the patient will be less likely to suffer from any possible adverse reactions to TFPI.

BRIEF DESCRIPTION OF THE DRAWINGS

FIG. 3A–B. Binding of $^{125}$I-TFPI to rat heptoma cells. A. Cells were incubated for 2 h at 4° C. with increasing concentrations of $^{125}$I-TFPI in the absence or presence of excess unlabelled TFPI or the 39-kDa protein. Total binding in the absence (●) or presence (○) of 500 nM 39-kDa protein was determined. Nonspecific binding (▲) was determined in the presence of a >400-fold molar excess of unlabelled TFPI. Specific binding (■) was derived as the difference between total and nonspecific TFPI binding. Symbols represent the means of duplicate determinations. Inset, Scatchard plot of specific binding. B, bound $^{125}$I-TFPI; B/F, bound/free $^{125}$I-TFPI. B. Inhibition of $^{125}$I-TFPI binding by unlabelled TFPI. Binding of $^{125}$I-TFPI (0.6 nM) was performed in the absence or presence of increasing concentrations of unlabelled TFPI. Each symbol represents the average of duplicate determinations.

DETAILED DESCRIPTION OF THE INVENTION

Figure 1:
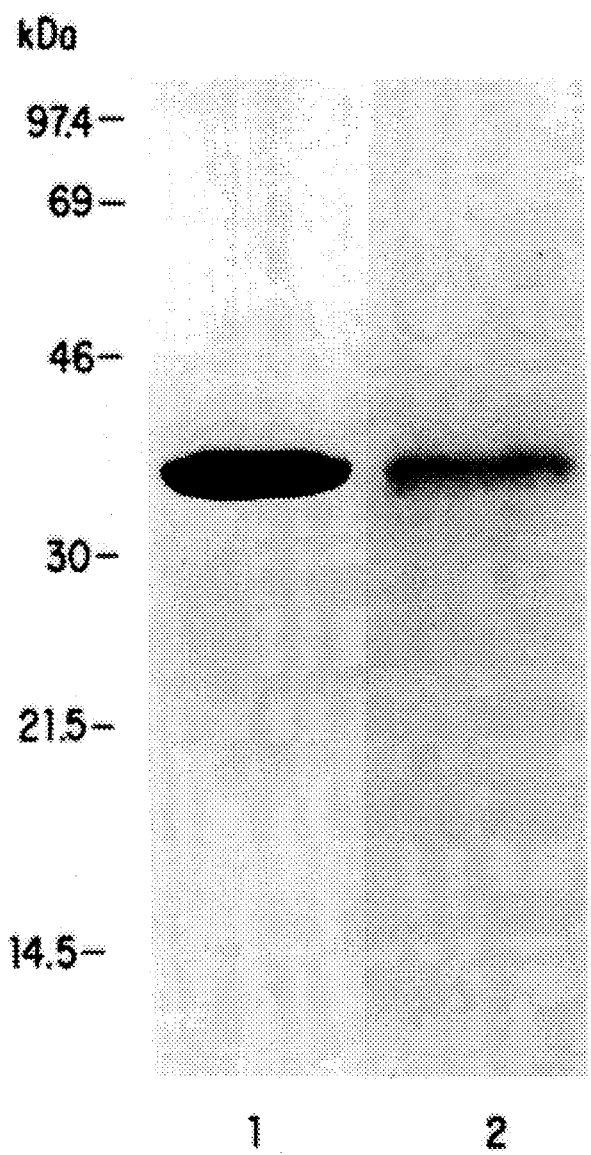
FIG. 1. 12.5% SDS-PAGE of recombinant TFPI and $^{125}$I-TFPI. Lane 1. 10 μg of purified TFPI was applied to a SDS-polyacrylamide gel and stained with Coomassie brilliant blue. Lane 2. ~20,000 cpm of $^{125}$I-TFPI was subjected to SDS-PAGE. The gel was dried and exposed to film for 18 h. Molecular weight markers in kDa are indicated on the left.

The present invention is the discovery that RAP reduces the hepatic clearance of TFPI. By binding to the hepatic clearance receptor for TFPI, RAP prevents TFPI from being bound to the receptor and removed from the circulating plasma and degraded via endocytosis. This increases the plasma half-life of TFPI thereby prolonging TFPI's therapeutic effectiveness. An increase in the plasma half-life of TFPI means that a smaller amount of TFPI may be used, which reduces the risk of adverse reaction to TFPI. Since TFPI is very expensive to produce, a significant cost savings can be achieved which, in turn, increases the availability of TFPI for clinical use.

RAP is an active, effective, competitive binding agent for the hepatic receptor for TFPI. This TFPI hepatic clearance-inhibiting protein is characterized by binding to LRP and inhibiting cellular degradation of TFPI via LRP up to 80–90%. Fragments of this 39kDa protein, particularly a 28kDa protein fragment, also inhibit TFPI cellular degradation. When RAP or a TFPI-hepatic clearance inhibiting fragment thereof is employed in the present invention, the standard dose of TFPI can be reduced.

Hepatic clearance of TFPI is inhibited in vivo in humans by administering a TFPI-hepatic clearance-inhibiting amount of RAP or a TFPI-hepatic clearance-inhibiting fragment thereof. The mode of administration is preferably intravenous. The preferred amount of RAP or fragment thereof administered to the human to inhibit hepatic clearance is in the range of about 60 to 6,000 mg/kg of body weight/dose. When the fragment of RAP is the 28kDa protein, the preferred amount administered to the human to inhibit hepatic clearance is in the range of about 38 to 3,800 mg/kg of body weight/dose. RAP or its fragments may be administered to the human concurrently with TFPI, but is preferably administered up to 20 minutes prior to the administration of TFPI. The reduction in hepatic clearance is measured by the increase in plasma half-life of TFPI.

It is to be understood that modified forms of RAP and fragments thereof which inhibit hepatic clearance of TFPI that are made by chemically or genetically modifying the amino acid sequence of RAP or fragments thereof are encompassed within the scope of the present invention. Such modified forms are characterized by their ability to bind to LRP and to reduce hepatic clearance of TFPI between 20 and 100%.

RAP, the 39kDa protein of the present invention, has the following amino acid sequence:

```
1               10                  20
Y S R E K N Q P K P S P K R E S G E E F R M E K L N Q L W 30              40                  50
E K A Q R L H L P P V R L A E L H A D L K I Q E R D E L A 60              70                  80
W K K L K L D G L D E D G E K E A R L I R N L N V I L A K 90              100                 110
Y G L D G K K D A R Q V T S N S L S G T Q E D G L D D P R
```

-continued

```
                120               130               140
      L E K L W H K A K T S G K F S G E E L D K L W R E F L H H
                150               160               170
      K E K V H E Y N V L L E T L S R T E E I H E N V I S P S D
                180               190               200
      L S D I K G S V L H S R H T E L K E K L R S I N Q G L D R
                210               220               230
      L R R V S H Q G Y S T E A E F E E P R V I D L W D L A Q S
                240               250               260
      A N L T D K E L E A F R E E L K H F E A K I E K H N H Y Q
                270               280
      K Q L E I A H E K L R H A E S V G D G E R V S R S R E K
      290               300               310
      H A L L E G R T K E L G Y T V K K H L Q D L S G R I S R
      A R
      320
      H N E L  [SEQ.ID.NO. 1]
```

Other aspects of the present invention are therapeutic compositions for treating the conditions referred to above. Such compositions comprise a therapeutically effective amount of TFPI and RAP in a mixture with a pharmaceutically acceptable carrier. This composition can be administered either parenterally, intravenously or subcutaneously. When administered, the therapeutic composition for use in this invention is preferably in the form of a pyrogen-free, parenterally acceptable aqueous solution. The preparation of such a parenterally acceptable protein solution, having due regard to pH, isotonicity, stability and the like, is within the skill of the art.

MATERIALS AND METHODS

Materials. Iodo-Gen was purchased from Pierce Chemical Co. [$^{125}$I] iodide was from Amersham Corp. Pronase was obtained from Calbiochem. Normal rabbit (nonimmune) IgG was purchased from Sigma. Protein A-agarose was from Repligen. Tissue culture media and plasticware were obtained from GIBCO/BRL.

Protein Purification. Recombinant human full-length TFPI was produced and purified from E. coli (27). U.S. Patents to Broze U.S. Pat. No. 5,106,833, to Wun et. al. U.S. Pat. No. 4,966,852, and to Diaz-Collier U.S. Pat. No. 5,212,091 disclose methods and genes for making TFPI and fragments thereof and can be referred to for additional details on how to make TFPI and fragments thereof. The resultant protein was homogenous as determined by SDS-PAGE. In FIG. 1 (lane 1) 10 µg of purified TFPI were electrophoresed on a SDS-polyacrylamide gel and stained with Coomassie brilliant blue. TFPI migrates as a single band with an apparent molecular weight of 35-kDa. TFPI (25–60 µg) was iodinated using the Iodo-Gen method (28). $^{125}$I-TFPI had a specific radioactivity generally of $2-8\times10^7$ cpm/µg of protein. The unincorporated $^{125}$I after gel-filtration purification over a PD-10 column was <2% of the total radioactivity. $^{125}$I-TFPI retained 88% of its functional activity (e.g. stoichiometric inhibition of factor Xa). FIG. 1 (lane 2) shows that $^{125}$I-TFPI also migrates at 35-kDa. Recombinant glutathione S-transferase (GST)-39-kDa fusion protein and GST-39-kDa fusion protein constructs were prepared and purified as described in references (25+ 26). The full-length GST-39-kDa fusion protein was cleaved with thrombin and the 39-kDa protein was purified by removing GST via heparin-agarose chromatography (25).

Antibodies. Polyclonal rabbit antibody was generated against purified human placental LRP described previously (22). Total IgG was purified using protein A-agarose.

Cell Culture. Rat hepatoma $MH_1C_1$ cells (21) and human hepatoma HepG2 cells (29) were cultured in Earle's minimum essential medium (with glutamine) supplemented with 10% fetal calf serum, 100 units/ml penicillin, and 100 µg/ml streptomycin (culture media). Cells were incubated at 37° C. in humidified air containing 5% $CO_2$.

Binding and Degradation Assays. $MH_1C_1$ cells were seeded into 12-well dishes two days prior to assay. Cell monolayers were generally used at 80–90% confluence. The cells were washed twice with 4° C. culture media and binding was initiated by adding 0.5 ml of culture media containing the indicated concentrations of $^{125}$I-TFPI in the absence or presence of competitor protein (unlabelled TFPI or 39-kDa protein). After incubation for 2 h at 4° C., the cells were washed three times with culture media and lysed in 62.5 mM Tris-HCl, pH 6.8, containing 0.2% (wt/vol) SDS and 10% (vol/vol) glycerol. Radioactivity of cell lysates was determined in a Packard gamma counter. Degradation assays were performed by washing cell monolayers twice with room temperature culture media. 0.5 ml of culture media containing 0.6 nM $^{125}$I-TFPI in the absence or presence of selected concentrations of the 39-kDa protein were then added to each well. After incubation at 37° C. for the indicated time periods, the overlying media were removed and precipitated by the addition of bovine serum albumin to 5 mg/ml and tricholoracetic acid to 20%. Degradation of ligand was defined as the appearance of radioactive ligand fragments in the overlying media that were soluble in tricholoracetic acid.

Single cycle endocytosis assays. Cells were seeded into 12-well dishes. After washing the cells twice with 4° C. culture media, 0.5 ml of culture media containing 0.6 nM $^{125}$I-TFPI in the absence or presence of 500 nM 39-kDa protein were added to each well. Nonspecific binding was determined in the presence of 500 nM unlabelled TFPI. After binding for 2 h at 4° C., cells were washed three times with 4° C. culture media to remove unbound ligand. Cells were then warmed rapidly to 37° C. by adding prewarmed culture media containing 200 nM unlabelled TFPI (to prevent $^{125}$I-TFPI rebinding) in the absence or presence of 500 nM 39-kDa protein. Following incubation at 37° C. for selected intervals, the overlying medium was removed and precipitated with trichloroacetic acid. The cell monolayers were washed three times with 4° C. phosphate-buffered saline (PBS) and incubated with PBS containing 0.25% Pronase for 30 min at 4° C. Cells were detached from the dishes by pipetting and separated from the buffer by centrifugation. Radioactivity of the supernatant fractions, defining cell surface ligand, was determined. Degradation of ligand was defined by the appearance of tricholoroacetic acid-soluble radioactivity in the overlying medium. The assay in HepG2 cells was similar to that in $MH_1C_1$ cells except cells were seeded into 24-well dishes. Cells were rinsed twice with 4° C. culture media and incubated with 0.2 ml of culture media containing 5 nM $^{125}$I-TFPI in the absence or presence of 500 nM unlabelled TFPI. After 2 h at 4° C. cells were washed three times with 4° C. culture media and rapidly warmed to 37° C. by adding prewarmed culture media containing 200 nM unlabelled TFPI in the absence or presence of 500 nM 39-kDa protein, 5 μM anti-LRP IgG, or 5 μM nonimmune IgG. Following incubation at 37° C. for selected intervals, the overlying medium was removed and subjected to tricholoroacetic acid precipitation.

EXAMPLE I

Purification of RAP

The procedure for purification of the 39kDa protein from strains of *E. coli* carrying the over-expression plasmid pGEX-39kDa has been described in Herz, J., Goldstein, J. L., Strickland, D. K., Ho, Y. K. & Brown, M. S. (1991) *J. Biol. Chem.* (24) A modified version of that procedure, described below, was employed.

Cultures of *E. coli*. strain DH5α carrying the over-expression plasmid pGEX-39kDa were grown to mid-log phase in LB medium with 100 μg/ml ampicillin at 37° C. Cultures were cooled to 30° C. and supplemented with 0.01% isopropylthio-β-D-galactoside to induce expression of the glutathione-S-transferase-39kDa fusion protein. Following a 4–6 hour induction at 30° C., cultures were cooled on ice and collected by centrifugation.

All of the following steps were carried out at 4° C. Cell pellets were lysed in PBSa containing 1% Triton X-100, 1 mM pepstatin, 2.5 μg/ml leupeptin, and 0.2 mM phenylmethylsulfonyl fluoride (PMSF). Sonication of this lysate was performed using a Branson Model 450 Sonifier, with the resulting membranes and other cellular debris collected by centrifugation at 15,000 g for 30 minutes. The supernatant from this step was incubated overnight with agarose immobilized glutathione beads (Sigma Chemical Co.). The beads were then washed, and elution of the fusion protein was carried out by competition with 5 mM reduced glutathione in 50 mm Tris, pH8 (Sigma Chemical Co.) Following dialysis, the fusion protein was cleaved by an overnight incubation with 100 ng of activated human thrombin per 50 μg of fusion protein. The glutathione-S-transferase epitope was subsequently removed by further incubation with agarose immobilized heparin beads.

The 28kDa protein fragment of RAP, has the following amino acid sequence:

```
1                    10                    20
P R L E K L W H K A K T S G K F S G E E L D K L W R E F L 30                   40                    50
H H K E K V H E Y N V L L E T L S R T E E I H E N V I S P S 60                   70                    80
D L S D I K G S V L H S R H T E L K E K L R S I N Q G L D R 90                   100                   110
L R R V S H Q G Y S T E A E F E E P R V I D L W D L A Q S A 120                  130                   140
N L T D K E L E A F R E E L K H F E A K I E K H N H Y Q K Q 150                  160                   170
L E I A H E K L R H A E S V G D G E R V S R S R E K H A L L 180                  190                   200
E G R T K E L G Y T V K K H L Q K L S G R I S R A R H N E L
```

[SEQ.ID.NO. 2]

The 28kDa protein is characterized by a molecular weight of 28,000 daltons on SDS-PAGE, stability to acid hydrolysis, solubility in 1% Triton X-100, and having approximately the same inhibitory activity ($K_i$) on TFPI cellular degradation via the hepatic receptor as the full-length 39kDa protein. The 28kDa protein has been cloned and purified as shown in the following example.

EXAMPLE 2

Cloning of the 28kDa Protein

The 28kDa protein is produced with a bacterial expression system according to Warshawsky et al (26). The gene encoding this protein is synthesized using polymerase chain reaction (PCR) with the following primers:

Forward: 'CGCGTGGATCCCCCAGGCTGGAAAAGCTGTGG3'
[SEQ.ID.NO. 3]
Reverse: ACGATGAATTCTCAGAGCTCATTGTGC-CGAGC
[SEQ.ID.NO. 4]. These PCR primers contain built-in restriction sites (BamH1 and EcoR1, respectively). The PCR product after restriction enzyme digestion is cloned directly to the pGEX-2T vector (Pharmacia). Other bacterial expression vectors may be used. The constructed plasmid is used to transform bacteria *E. coli* strain DH5α and this bacterial transformant bearing the recombinant plasmid is used to produce the 28kDa protein using the procedure of Example 1.

Using standard recombinant techniques, a chemically synthesized gene encoding the 28kDa protein may be prepared. The chemically synthesized gene comprises a chemically synthesized polynucleotide which codes on expression for the amino acid sequence of the 28kDa protein given above.

A 39kDa rat protein which binds to LRP and also inhibits the cellular degradation of TFPI via LRP. The 28kDa protein of this rat protein has the following amino acid sequence:

```
1                   10                  20
P R L E K L W H K A K T S G S V R L T S C A R V L H K E K
30                  40                  50
I H E Y N V L L D T L S R A E E G Y E N L L S P S D M T H I
60                  70                  80
K S D T L A S K H S E L K D R L R S I N Q G L D R L R K V S
90                  100                 110
H Q L R P A T E F E E P R V I D L W D L A Q S A N F T E K E
120                 130                 140
L E S F R E E L K H F E A K I E K H N H Y Q K Q L E I S H Q
150                 160                 170
K L K H V E S I G D P E H I S R N K E K Y V L L E E K T K E
180                 190                 200
L G Y K V K K H L Q D L S S R V S R A R H N E L
```
[SEQ.ID.NO. 5]

Using standard recombinant techniques, a chemically synthesized gene encoding this rat protein may be prepared. The chemically synthesized gene comprises a chemically synthesized polynucleotide which codes on expression for the amino acid sequence of the rat protein given above.

EXAMPLE 3

Inhibition of $^{125}$I-TFPI degradation by 39kDa protein.

Figure 2A:
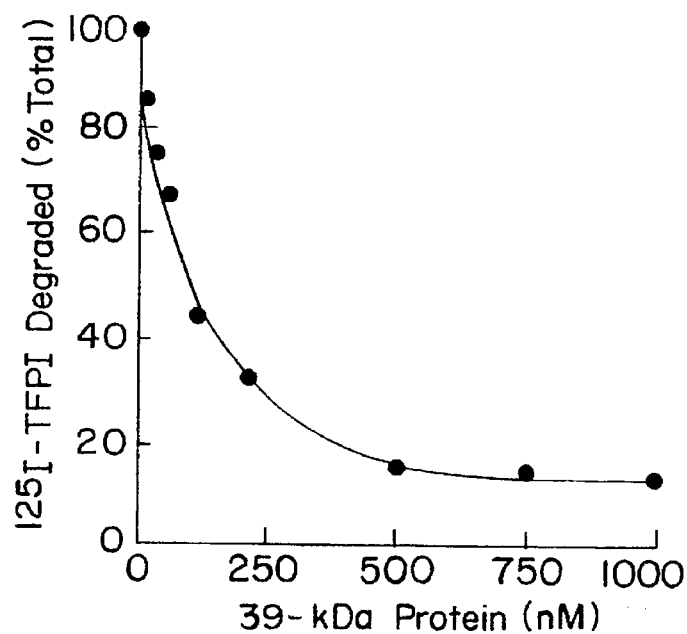
FIG. 2A–B. Inhibition of $^{125}$I-TFPI degradation by the 39-kDa protein on rat hepatoma cells. A. Cells were incubated at 37° C. for 4 h with 0.6 nM $^{125}$I-TFPI in the absence or presence of increasing concentrations of the 39-kDa protein. Thereafter, buffers overlying the cell monolayers were subjected to trichloroacetic acid precipitation, and trichloroacetic acid-soluble radioactivity, representing degraded ligand, was determined. TFPI degraded in the absence of any 39-kDa protein was defined as 100%. Each symbol represents the average of duplicate determinations. B. Cells were incubated with 0.6 nM $^{125}$I-TFPI at 37° C. for the indicated periods of time in the absence (○) or presence (●) of 500 nM 39-kDa protein. At the indicated times, buffers overlying the cell monolayers were subjected to trichloroacetic acid precipitation. The radioactivity was normalized to femtomole equivalents of TFPI calculated from the specific activity of $^{125}$I-TFPI. Each symbol represents the average of duplicate determinations.
Figure 2B:
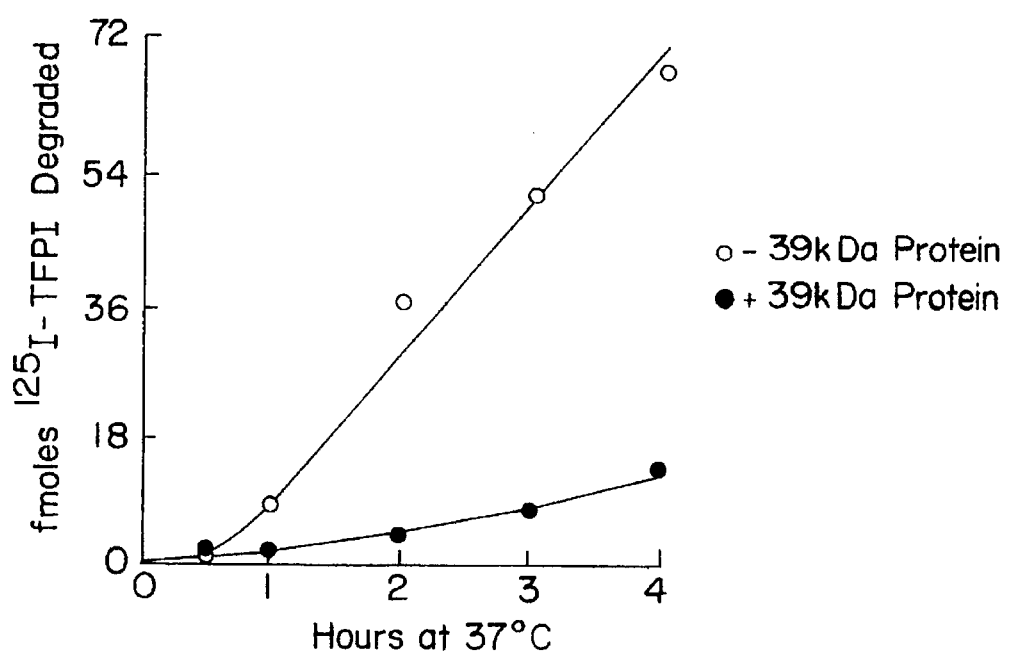

To investigate whether rat hepatoma $MH_1C_1$ cells were capable of mediating the cellular degradation of TFPI and to determine whether LRP was involved in this process, $MH_1C_1$ cells were incubated with 0.6 nM $^{125}$I-TFPI in the absence or presence of the LRP-associated 39kDa protein for 4 h at 37° C. Thereafter buffer overlying the cell monolayers was subjected to trichloracetic acid precipitation and tricholoroacetic acid-soluble radioactivity, representing degraded ligand, was determined. FIG. 2A demonstrates that the 39-kDa protein inhibits $^{125}$I-TFPI degradation in a dose-dependent manner with a $K_i$ value$^2$ of ~100 nM. At the maximum dose of 39-kDa protein added, 1000 nM, 80% of total $^{125}$I-TFPI degradation was inhibited. Similar results were obtained with human hepatoma HepG2 cells (data not shown). FIG. 2B demonstrates a time course for $^{125}$I-TFPI degradation in the absence or presence of 500 nM 39-kDa protein. In the absence of the 39-kDa protein, degradation of $^{125}$I-TFPI (initial concentration of 0.6 nM) increased linearly for at least 4 h. When the 39-kDa protein was included in the incubation, $^{125}$I-TFPI degradation was inhibited by ~80%. These results strongly suggest that LRP mediates the cellular degradation of $^{125}$I-TFPI.

EXAMPLE 4

Binding of $^{125}$I-TFPI to $MH_1C_1$ cells in the absence or presence of 39kDa protein.

To investigate whether TFPI bound to LRP prior to its uptake and degradation, saturation binding experiments were performed with $^{125}$I-TFPI on $MH_1C_1$ cells in the absence or presence of the 39-kDa protein. Binding studies were performed at 4° C. to avoid possible ligand uptake and degradation. As shown in FIG. 3A, $^{125}$I-TFPI bound specifically to $MH_1C_1$ cells over the concentration range of 0.6–12 nM. Nonspecific binding, determined in the presence of a >400-fold molar excess of unlabelled TFPI, increased linearly and accounted for 20% of total $^{125}$I-TFPI binding.

Saturation of specific binding was not reached at a $^{125}$I-TFPI concentration of 12 nM. Scatchard analysis (30) of the binding data yielded approximately $2\times10^6$ binding sites/cell with an apparent $K_d$ of ~15 nM (inset, FIG. 3A). In FIG. 3B, the inhibition of $^{125}$I-TFPI binding by increasing concentrations of unlabelled TFPI was examined. As seen, unlabelled TFPI competes with 0.6 nM $^{125}$I-TFPI binding in a dose-dependent manner with a $K_i$ value of 50 nM. The data in FIGS. 3A and 3B yield an average $K_d$ value of ~30 nM. FIG. 3A also shows that the presence of 500 nM 39-kDa protein has no apparent effect on $^{125}$I-TFPI binding, indicating that the primary TFPI binding site on $MH_1C_1$ cells is not LRP.

EXAMPLE 5

Single cycle endocytosis of $^{125}$I-TFPI in the absence and presence of 39kDa PROTEIN.

Figure 4A:
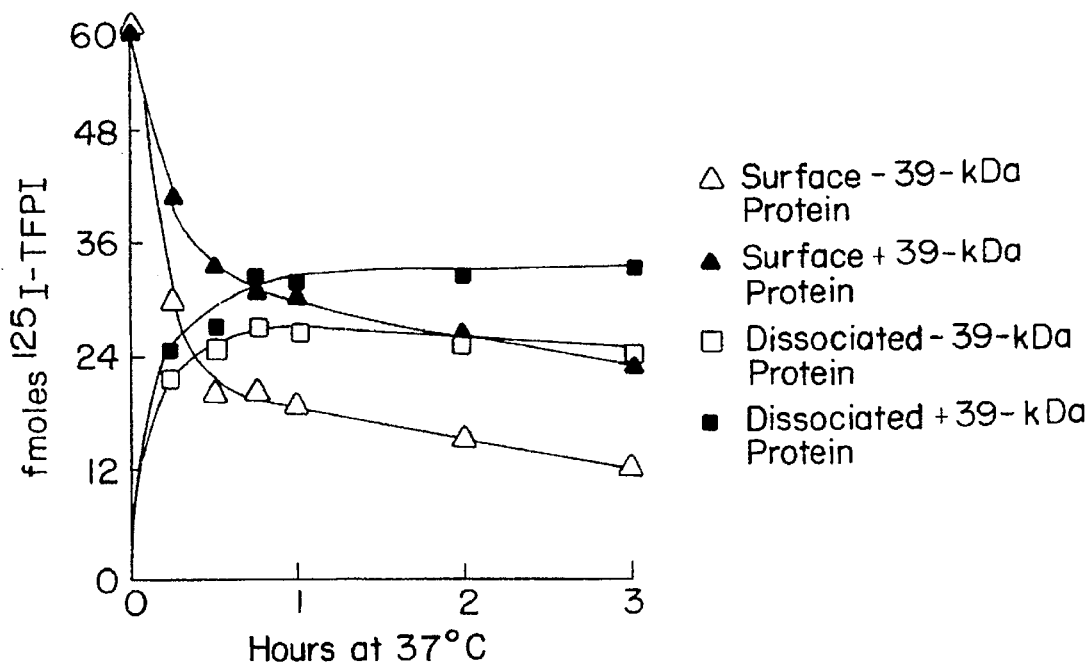
FIG. 4A–B. Distribution of $^{125}$I-TFPI during a single cycle of endocytosis in rat hepatoma cells in the absence and presence of the 39-kDa protein. Cells were incubated with 0.6 nM $^{125}$I-TFPI in the absence or presence of 500 nM unlabelled TFPI or 500 nM 39-kDa protein for 2 h at 4° C. After washing to remove unbound ligand, cells were incubated at 37° C. for selected intervals with 200 nM unlabelled TFPI in the absence or presence of 500 nM 39-kDa protein. The overlying media was removed and the cells were chilled on ice and rinsed prior to treatment with Pronase. A. Cell-surface $^{125}$I-TFPI (Pronase-sensitive) in the absence (Δ) and presence (▲) of the 39-kDa protein was determined. Dissociated $^{125}$I-TFPI (tricholoracetic acid-precipitable) in the absence (□) and presence (■) of the 39-kDa protein was quantified. B. Degraded $^{125}$I-TFPI (trichloroacetic acid-soluble) in the absence (○) and presence (●) of the 39-kDa protein is indicated. Absolute amounts of cell-surface, dissociated, and degraded ligand were normalized to femtomole equivalents of TFPI calculated from the specific activity of $^{125}$I-TFPI. Symbols represent the specific signals (difference in the absence and presence of unlabelled ligand) and are the means of duplicate determinations.
Figure 4B:
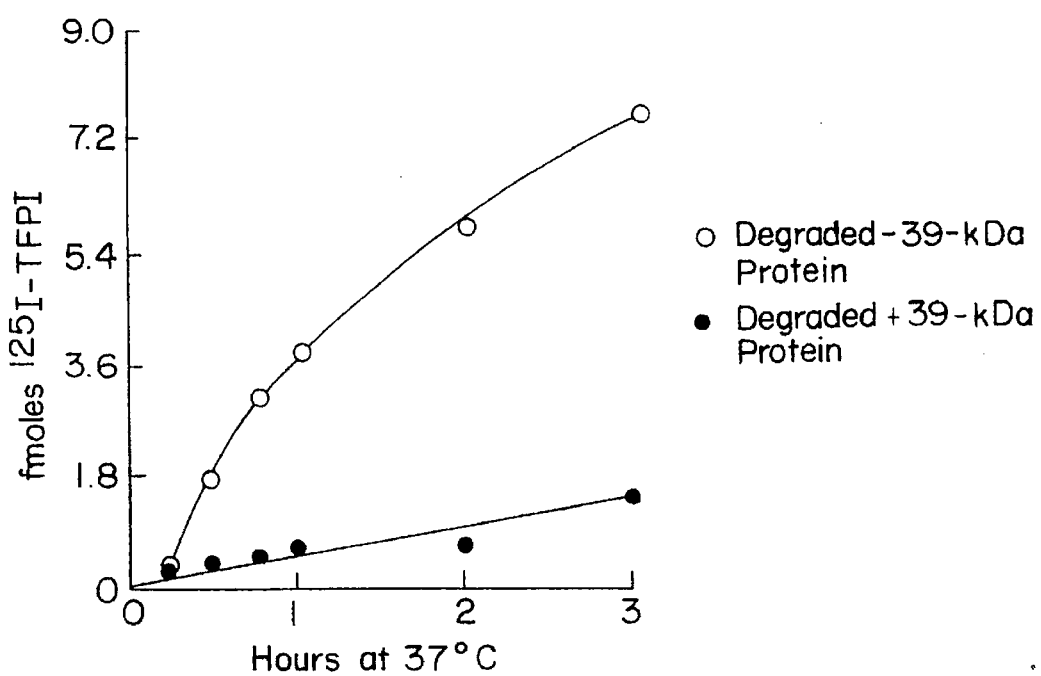

To define the location of $^{125}$I-TFPI during a single cycle of endocytosis in $MH_1C_1$ cells, the subsequent fate of a pre-bound cohort of TFPI molecules was examined. $^{125}$I-TFPI was incubated with $MH_1C_1$ cells for 2 h at 4° C. in the absence or presence of 39kDa protein to allow cell surface binding. After removal of unbound ligand, ligand uptake was initiated by incubating cells at 37° C. for selected intervals with excess unlabelled TFPI (to prevent $^{125}$I-TFPI rebinding) in the absence or presence of 39kDa protein. At selected intervals, the overlying media were removed and subjected to trichloroacetic acid precipitation. The cell monolayers were quickly cooled to stop further ligand internalization, rinsed, and treated with Pronase at 4° C. to remove residual surface ligand. $^{125}$I-TFPI bound to the cell surface underwent two fates: As seen in FIG. 4A, upon warming the cells to 37° C., approximately 50% of specifically bound $^{125}$I-TFPI dissociated from the cell surface within 15 min and accumulated in the overlying media. 39kDa protein did not significantly affect this process. The rapid dissociation of TFPI from the cell surface is consistent with its' low affinity binding to $MH_1C_1$ cells ($K_d$ ~30 nM). FIG. 4B demonstrates that a smaller fraction (approximately 10%) of cell surface bound $^{125}$I-TFPI was taken into the cell

EXAMPLE 6

Figure 6:
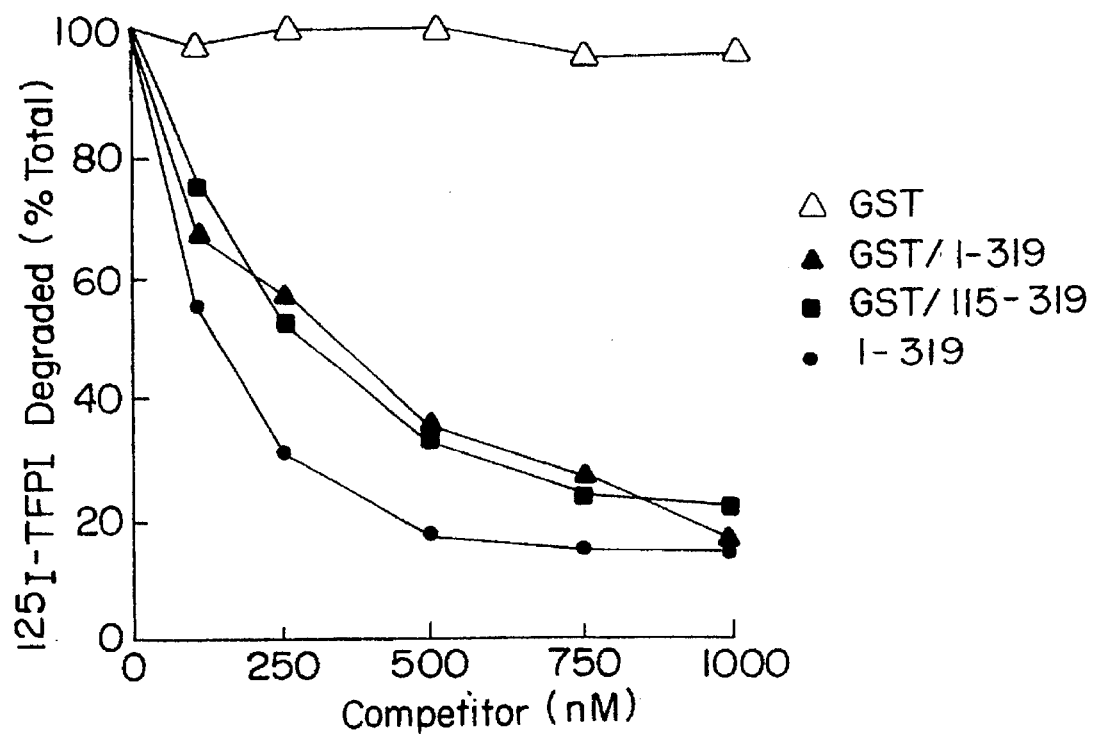
FIG. 6. Inhibition of $^{125}$I-TFPI degradation by 39-kDa protein constructs on rat hepatoma cells. Cells were incubated at 37° C. for 4h with 0.6 nM $^{125}$I-TFPI in the absence or presence of increasing concentrations of GST/1–319(▲), GST/115–319(■), 1–319(●), and as a negative control, GST (Δ). Thereafter, buffers overlying the cell monolayers were subjected to trichloracetic acid precipitation, and trichloroacetic acid-soluble radioactivity, representing degraded ligand, was determined. $^{125}$I-TFPI degraded in the absence of any competitor protein was defined as 100%. Each symbol represents the average of duplicate determinations.

Inhibition of $^{125}$I-TFPI degradation by 39kDa protein constructs on rat hepatoma cells To define whether portions of the 39kDa protein were capable of inhibiting $^{125}$I-TFPI degradation, a 28kDa fragment containing amino acid residues 115-319 of the 39kDa protein was generated as a fusion protein with GST. The resultant construct, GST/115-319, was examined for its ability to inhibit $^{125}$I-TFPI degradation, when compared to the full-length 39kDa protein (1-319), the full length 39kDa fusion protein (GST/1-319) or GST alone. As seen in FIG. 6, the 28kDa construct is as effective as the full-length protein construct in inhibition of $^{125}$I-TFPI cellular degradation.

EXAMPLE 7

Effect of anti-LRP IgG on the degradation of $^{125}$I-TFPI by HepG2 cells.

The applicants have demonstrated that LRP mediates the cellular degradation of TFPI in hepatoma cells since this process is inhibited by both antibodies directed against LRP and by RAP. The data also suggest that while LRP mediates the cellular degradation of TFPI, the initial TFPI binding site on hepatocytes is not LRP. Two lines of evidence support this conclusion: First, RAP, an inhibitor of ligand interactions with LRP, does not inhibit TFPI binding to hepatoma cells at 4° C. $MH_1C_1$ cells appear to have about 10 times as many TFPI binding sites ($2\times10^6$) as binding sites for the LRP-specific ligands t-PA (28,31), $\alpha_2M^*$ (Bu et al., unpublished observation), and the 39-kDa protein (31) ($0.1-0.5\times 10^6$) It is possible that a small fraction of the TFPI binding sites are inhibited by RAP but this is below the sensitivity of the assay. If a fraction of cell surface TFPI binding was to LRP, this TFPI would be internalized and degraded when the cells were warmed to 37° C. Since ~10% of cell surface bound TFPI was degraded at 37° C. in a RAP inhibitable manner (FIG. 4B), this may imply TFPI does bind to LRP on hepatoma cells. Alternatively it is possible that TFPI initially binds to another cell surface molecule and is transferred to LRP for uptake and degradation. A second line of evidence that suggests LRP is not the initial TFPI binding site is that the average $K_d$ value for TFPI binding to hepatoma cells is ~30 nM which is an approximately 10-fold lower affinity than has been observed for the binding of LRP-specific ligands to LRP. For example we reported that the $K_d$ value for t-PA and RAP binding to LRP on $MH_1C_1$ cells was ~3-6 nM (28,31). Williams et al. (32) reported that the 39-kDa protein (recombinant RAP) bound to purified LRP with a $K_d$ value of 4 nM. Moestrup and Gliemann demonstrated (33) that $\alpha_2M^*$ bound to purified LRP with two affinities ($K_d$ values of 40 pM and 2 nM). It is interesting to note that Callander et al. (34), using human ovarian carcinoma cell lines, observed $\sim0.3\times10^6$ TFPI binding sites/cell with an average $K_d$ value of 4.5 nM. The differences in the number of binding sites/cell and $K_d$ value we observed from what Callander found may reflect differences in the TFPI used and/or differences in the cell lines.

Several ligands for LRP mediated endocytosis/degradation are initially bound to other cell surface molecules prior to their uptake and degradation by LRP. In monocytes (35), u-PA:PAI-1 complexes initially bind to the glycosyl-phosphatidyl- inositol anchored u-PA receptor since u-PA:PAI-1 complex binding is not inhibited by the 39-kDa protein but is inhibited by the amino-terminal fragment of u-PA, a 16-kDa portion of u-PA which binds to the u-PA receptor as well as u-PA itself (36). Following binding, u-PA:PAI-1 complexes are thought to be transferred from the u-PA receptor to LRP for internalization and degradation since this process is inhibited by both the 39-kDa protein and by polyclonal anti-LRP antibodies (35).

Heparan sulfate proteoglycans (HSPG) constitute a second class of cell-surface binding proteins that present ligands to LRP for uptake and degradation. Using CHO cell mutants deficient in or lacking cell surface HSPG and by pretreating HepG2 cells with heparinase, Ji et al. (37) demonstrated that HSPG serve as the initial binding site for apoE-enriched βVLDL. Since LRP can mediate the uptake of apoE-enriched βVLDL (15), it has been proposed that HSPG bind apoE-enriched βVLDL on the cell surface and present these lipoproteins to LRP for internalization and degradation (37).

Lipoprotein lipase (LPL) is a triglyceride hydrolase that plays a key role in lipoprotein metabolism (38). LPL shares several of the same properties as TFPI: In plasma both LPL (39) and TFPI (4,5) are associated with lipoproteins. LPL and TFPI are both heparin binding proteins and after intravenous administration of heparin, plasma levels of both are increased several fold (6,7,40). LPL enhances the binding of lipoproteins to heparan sulfate both on the cell surface and in the extracellular matrix (41). LPL also enhances the binding of apoE-enriched lipoproteins to LRP on fibroblasts (42). LPL binds to purified LRP (23,43). However in intact fibroblasts (43), degradation of LPL, but not surface binding, is blocked by antibodies directed against LRP. Taken together these results have suggested that HSPG are involved in presenting LPL to LRP for uptake and degradation. A similar model may exist for TFPI whereby HSPG or some other, as yet unidentified, cell surface molecule binds TFPI and presents TFPI to LRP for uptake and degradation.

Figure 5:
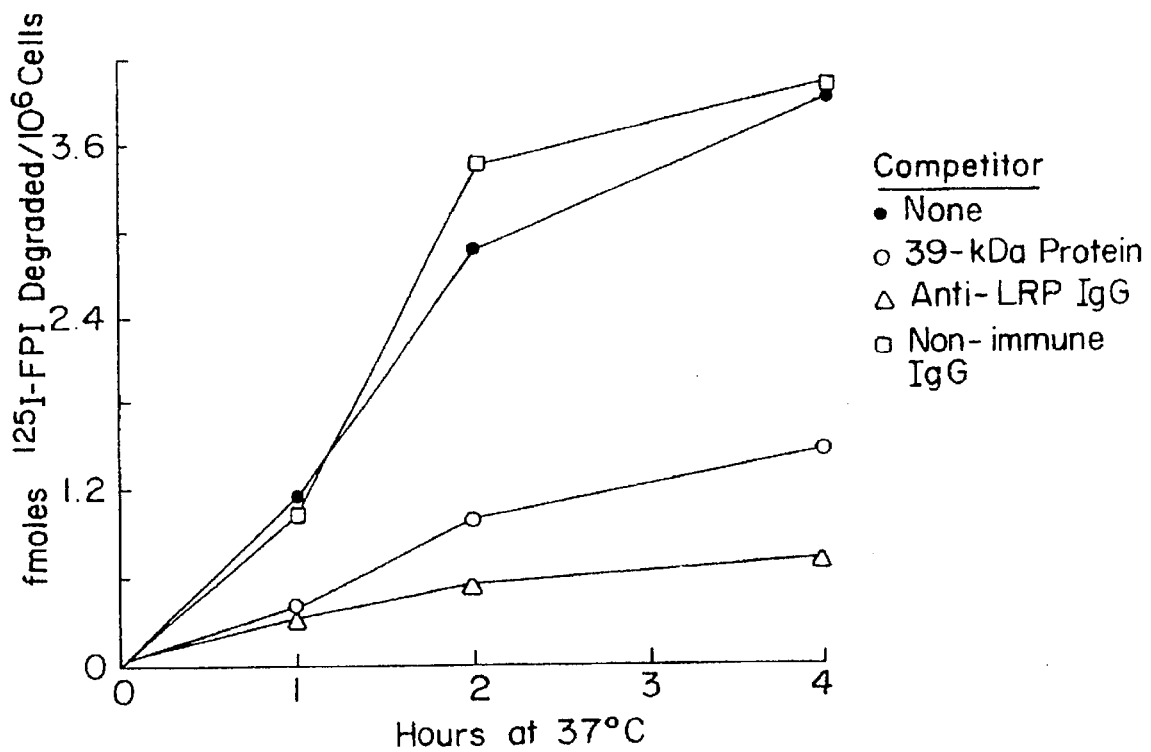
FIG. 5. Inhibition of $^{125}$I-TFPI degradation by anti-LRP IgG on human heptaoma cells. Cells were incubated with 0.6 nM $^{125}$I-TFPI in the absence or presence of 500 nM unlabelled TFPI at 4° C. for 2 h to allow surface binding. After washing, cells were incubated at 37° C. for selected intervals with 200 nM unlabelled TFPI in the absence or presence of 5 μM anti-LRP IgG, 5 μM nonimmune IgG or 500 nM 39-kDa protein. The overlying buffer was then removed and precipitated with trichloroacetic acid. Degraded $^{125}$I-TFPI in the absence (●) or presence of anti-LRP IgG (Δ), nonimmune IgG (□), and the 39-kDa protein (○) was determined. Symbols represent the specific signals (difference in the absence and presence of unlabelled TFPI) and are means of duplicate or triplicate determinations.

In vivo many LRP specific ligands are rapidly cleared by the liver including LPL (44), $\alpha_2M^*$ (45), apoE-enriched chylomicron remnants (46), t-PA (46), u-PA (48) and the 39-kDa protein (25). The 39-kDa protein is also cleared by the kidney where gp330 may mediate its' clearance (25). gp330 has also been implicated in the clearance of LPL (49) and u-PA:PAI-I complexes (14). Since the sites of TFPI clearance are also the liver and kidney (11), it seems likely that TFPI clearance in vivo may be mediated by LRP and gp330. To test whether degradation of TFPI was mediated directly by LRP, the effect of antibodies directed against LRP on TFPI degradation was examined. Human hepatoma HepG2 cells were used in this experiment since our LRP antibody was prepared against human LRP (22). $^{125}$I-TFPI was incubated with HepG2 cells for 2 h at 4° C. Following removal of unbound ligand, ligand uptake was initiated by incubating the cells at 37° C. in the absence or presence of competitor IgG (anti-LRP and nonimmune) or the 39-kDa protein. At selected intervals, the overlying media were removed and precipitated with trichloroacetic acid. As seen in FIG. 5, $^{125}$I-TFPI degradation increased over 4 h. Anti-LRP IgG specifically inhibited this degradation by ~80% while nonimmune IgG had no effect. FIG. 5 also shows that the 39-kDa protein inhibited ~65% of $^{125}$I-TFPI degradation in HepG2 cells.

Various other examples will be apparent to the person skilled in the art after reading the present disclosure without departing from the spirit and scope of the invention. It is intended that all such other examples be included within the scope of the appended claims.

TFPI is intended to be defined as not only as the full length molecule but also as fragments and/or variants thereof. In addition to full length TFPI and fragments thereof as has been disclosed above WO/91/02753 issued as EP patent 931201 discloses additional variants.

All references, patents or applications cited herein are incorporated by reference in their entirety as if written herein.

REFERENCES

1. Broze, G. J., Jr. (1992) *Seminars in Hematology* 29, 159–169.
2. Broze, G. J., Jr. & Tollefsen, D. M. (1993) Regulation of blood coagulation by protease inhibitors. In *The Molecular Basis of Blood Diseases*, Second Edition, W. B. Saunders Company. Philadelphia. pp. 629–656.
3. Novotny, W. F., Brown, S. G., Miletich, J. P., Rader, D. J. & Broze, G. J., Jr. (1991) *Blood* 78, 387–393.
4. Hubbard, A. R. & Jennings, C. A. (1987) *Thromb. Res.* 46, 527–537.
5. Novotny, W. F., Girard, T. J., Miletich, J. P. & Broze, G. J., Jr. (1989) *J. Biol. Chem.* 264, 18832–18837.
6. Novotny, W. F., Palmier, M. O., Wun, T. -C., Broze, G. J., Jr. & Miletich, J. P. (1991) *Blood* 78, 394–400.
7. Sandset, P. M., Abildgaard, U. & Larsen, M. L. (1988) *Thromb. Res.* 50, 803–813.
8. Day, K. C., Hoffman, L. C., Palmier, M. O., Kretzmer, K. K., Huang, M. D., Pyla, E. Y., Spokas, E., Broze, G. J., Jr., Warren, T. G. & Wun, T.- C. (1990) *Blood* 76, 1538–1545.
9. Haskel, E. J., Torr, S. R., Day, K. C., Palmier, M. O., Wun, T. -C., Sobel, B. E. & Abendschein, D. R. (1991) *Circulation* 84, 821–827.
10. Creasey, A. A., Chang, A. C. K., Feigen, L., Wun, T.- C., Taylor, F. B., Jr. & Hinshaw, L. B. (1993) *J. Clin. Invest.* 91, 2850–2860.
11. Palmier, M. O., Hall, L. J., Reisch, C. M., Baldwin, M. K., Wilson A. G. E. & Wun, T.-C. (1992) *Thromb. Haemostas.* 68, 33–36.
12. Brown, M. S., Herz, J., Kowal, R. C. & Goldstein, J. L. (1991) *Curr. Opin. Lipidology* 2, 65–72.
13. Willnow, T. E., Goldstein, J. L., Orth, K., Brown, M. S. & Herz, J. (1992) *J. Biol. Chem.* 267, 26172–26180.
14. Moestrup, S. K., Nielsen, S., Andreasen, P., Jorgensen, K. E., Nykjaer, A., Roigaard, H., Gliemann, J. & Christensen, E. I. (1993) *J. Biol. Chem.* 268, 16564–16570.
15. Kowal, R. C., Herz, J., Goldstein, J. L., Esser, V. & Brown, M. S. (1989) *Proc. Natl. Acad. Sci.* 86, 5810–5814.
16. Ashcom, J. D., Tiller, S. E., Dickerson, K., Cravens, J. L., Argraves, W. S. & Strickland, D. K. (1990) *J. Cell Biol.* 110, 1041–1048.
17. Moestrup, S. K. & Gliemann, J. (1991) *J. Biol. Chem.* 266, 14011–14017.
18. Williams, S., Ashcom, J. D., Argraves, W. S., and Strickland, D. K. (1992) *J. Biol. Chem.* 267, 9035–9040.
19. Kounnas, M. Z., Morris, R. E., Thompson, M. R., Fitzgerald, D. J., Strickland, D. K. & Saelinger, C. B. (1992) *J. Biol. Chem.* 267, 12420–12423.
20. Kounnas, M. Z., Argraves, W. S. & Strickland, D. K. (1992) *J. Biol. Chem.* 267, 21162–21166.
21. Bu, G., Williams, S., Strickland, D. K. & Schwartz, A. L. (1992) *Proc. Natl. Acad. Sci. USA* 89, 7427–7431.
22. Bu, G., Maksymovitch, E. A. & Schwartz, A. L. (1993) *J. Biol. Chem.* 268, 13002–13009.
23. Nykjaer, A., Bengtsson-Olivecrona, G., Lookene, A., Moestrup, S. K., Petersen, C. M., Weber, W., Beisiegel, U. & Gliemann, J. (1993) *J. Biol. Chem.* 268, 15048–15055.
24. Herz, J., Goldstein, J. L., Strickland, D. K., Ho, Y. K. & Brown, M. S. (1991) *J. Biol. Chem.* 266, 21232–21238.
25. Warshawsky, I., Bu, G. & Schwartz, A. L. (1993) *J. Clin. Invest.* 92, 937–944.
26. Warshawsky, I, Bu, G & Schwartz, A. L.(1993), *J. Biol. Chem.*, 268, 22046–22054.
27. Huang, Z.-H., Wun, T.-C. & Broze, G. J. Jr. (1993) *J. Biol. Chem.* 268, 26950–26955.
28. Bu, G., Morton, P. A. & Schwartz, A. L. (1992) *J. Biol. Chem.* 267, 15595–15602.
29. Schwartz, A. L., Fridovich, S. E., Knowles, B. B. & Lodish, H. F. (1981) *J. Biol. Chem.* 256, 8878–8881.
30. Scatchard, G. (1949) *Ann. N. Y. Acad. Sci.* 51, 660–672.
31. Iodonato, S. P., Bu, G., Maksymovitch, E. A. & Schwartz, A. L. (1993) *Biochem J.*, 296, 867–875
32. Williams, S. E., Ashcom, J. D., Argraves, W. S. & Strickland, D. K. (1992) *J. Biol. Chem.* 267, 9035–9040.
33. Moestrup, S. K. & Gliemann, J. (1991) *J. Biol. Chem.* 266, 14011–14017.
34. Callander, N. S., Rao, L. V. M., Nordfang, O., Sandset, P. M., Warn-Cramer, B. & Rapaport, S. I. (1992) *J. Biol. Chem.* 267, 876–882.
35. Nykjaer, A., Petersen, C. M., Moller, B., Jensen, P. H., Moestrup, S. K., Holtet, T. L., Etzerodt, M., Thogersen, H. C., Munch, M., Andreasen, P. A. & Gliemann, J. (1992); *J. Biol. Chem.* 267, 14543–14546.
36. Stoppelli, M. P., Corti, A., Soffientini, A., Cassani, G., Blasi, F. & Assoia, N. (1985) *Proc. Natl. Acad. Sci. USA* 82, 4939–4943.
37. Ji, Z.-S., Brecht, W. J., Miranda, R. D., Hussain, M. M., Innerarity, T. L. & Mahley, R. W. (1993) *J. Biol. Chem.* 268, 10160–10167.
38. Bensadoun, A. (1991) *Annu. Rev. Nutr.* 11, 217–237.
39. Goldberg, I. J., Kandel, J. J., Blum, C. B. & Ginsberg, H. N. (1986) *J. Clin. Invest.* 78, 1523–1528.
40. Kern, P. A., Martin, R. A., Carry, J., Goldberg, I. J. & Ong, J. M. (1990) *J. Lipid Res.* 31, 17–26.
41. Eisenberg, S., Sehayek, E., Olivecrona, T. & Vlodavsky, I. (1992) *J. Clin. Invest.* 90, 2013–2121.
42. Beisiegel, U., Weber, W. & Bengtsson-Olivecrona, G. (1991) *Proc. Natl. Acad. Sci. USA* 88, 8342–8346.
43. Chappell, D. A., Fry, G. L., Waknitz, M. A., Iverius, P.-H., Williams, S. E. & Strickland, D. K. (1992) *J. Biol. Chem.* 267, 25764–25767.
44. Wallinder, L., Peterson, J., Olivecrona, T. & Bengtsson-Olivecrona, G. (1984) *Biochim. et Biophys. Acta* 795, 513–524.
45. Fuchs, H. E., Shifman, M. A. & Pizzo, S. V. (1982) *Biochim. et Biophys. Acta* 716, 151–157.
46. Brown, M. S. & Goldstein, J. L. (1983) *J. Clin. Invest.* 72, 743–747.
47. Emeis, J. J., Van den Hoogen, C. M. & Jense, D. (1985) *Thromb. Haemostas.* 54, 661–664.
48. Collen, D., De Cock, F. & Lijnen, H. R. (1984) *Thromb. Haemostas.* 52, 24–26.
49. Kounnas, M. Z., Chappell, D. A., Strickland, D. K. & Argraves W. S. (1993) *J. Biol. Chem.* 268, 14176–14181.

What is claimed is:

1. A method of inhibiting the hepatic clearance of tissue factor pathway inhibitor (TFPI) in a mammal comprising administering said TFPI to a mammal in need thereof; and inhibiting clearance of said TFPI by administering an effective amount of a polypeptide having the sequence selected from the group consisting of:

YSREKNQPKPSPKRESGEEFRMEKLNQLW [SEQ. ID. NO. 1]
EKAQRLHLPPVRLAELHADLKIQERDELA
WKKLKLDGLDEDGEKEARLIRNLNVILAK
YGLDGKKDARQVTSNSLSGTQEDGLDDPR
LEKLWHKAKTSGKFSGEELDKLWREFLHH
KEKVHEYNVLLETLSRTEEIHENVISPSD
LSDIKGSVLHSRHTELKEKLRSINQGLDR
LRRVSHQGYSTEAEFEEPRVIDLWDLAQS
ANLTDKELEAFREELKHFEAKIEKHNHYQ
KQLEIAHEKLRHAESVGDGERVSRSREK
HALLEGRTKELGYTVKKHLQDLSGRISRAR
HNEL; and -continued PRLEKLWHKAKTSGKFSGEELDKLWREFL [SEQ. ID. NO. 2]
HHKEKVHEYNVLLETLSRTEEIHENVISPS
DLSDIKGSVLHSRHTELKEKLRSINQGLDR
LRRVSHQGYSTEAEFEEPRVIDLWDLAQSA
NLTDKELEAFREELKHFEAKIEKHNHYQKQ
LEIAHEKLRHAESVGDGERVSRSREKHALL
EGRTKELGYTVKKHLQKLSGRISRARHNEL.

2. The method of claim 1 wherein said polypeptide is administered 0 to 20 minutes before TFPI is administered.

3. The method of claim 1 wherein said polypeptide inhibits TFPI hepatic clearance by between 20 and 100 percent.

4. The method of claim 1 wherein said TFPI is full length TFPI.

5. A pharmaceutical composition, comprising:

tissue factor pathway inhibitor (TFPI);

a polypeptide having the sequence selected from the group consisting of:

YSREKNQPKPSPKRESGEEFRMEKLNQLW

EKAQRLHLPPVRLAELHADLKIQERDELA

WKKLKLDGLDEDGEKEARLIRNLNVILAK

YGLDGKKDARQVTSNSLSGTQEDGLDDPR

LEKLWHKAKTSGKFSGEELDKLWREFLHH

KEKVHEYNVLLETLSRTEEIHENVISPSD

LSDIKGSVLHSRHTELKEKLRSINQGLDR

LRRVSHQGYSTEAEFEEPRVIDLWDLAQS

ANLTDKELEAFREELKHFEAKIEKHNHYQ

KQLEIAHEKLRHAESVGDGERVSRSREK

HALLEGRTKELGYTVKKHLQDLSGRISRAR

HNEL [SEQ.ID.NO. 1]; and

PRLEKLWHKAKTSGKFSGEELDKLWREFL

HHKEKVHEYNVLLETLSRTEEIHENVISPS

DLSDIKGSVLHSRHTELKEKLRSINQGLDR

LRRVSHQGYSTEAEFEEPRVIDLWDLAQSA

NLTDKELEAFREELKHFEAKIEKHNHYQKQ

LEIAHEKLRHAESVGDGERVSRSREKHALL

EGRTKELGYTVKKHLQKLSGRISRARHNEL

[SEQ.ID.NO. 2]; and a pharmaceutically- acceptable carrier.

6. The pharmaceutical composition of claim 5 wherein said TFPI is full length TFPI.

* * * * *